United States Patent [19]

Alegre et al.

[11] Patent Number: 5,162,095
[45] Date of Patent: Nov. 10, 1992

[54] METHOD AND INSTALLATION FOR THE ANALYSIS BY NEUTRON ACTIVATION OF A FLOW OF MATERIAL IN BULK

[75] Inventors: Rene Alegre, Rueil Malmaison; Jacques L. E. Alexandre, Les Sorinieres; Thierry M. M. Barnavon, Bouguenais; Jean-Pierre N. Baron, La Montagne; Jacques Cariou, Roven; Leon Debray, Noisy-Le-Roi, all of France

[73] Assignees: Etat Francais, Paris; Ciments Lafarge, Saint-Cloud, both of France

[21] Appl. No.: 824,898

[22] Filed: Jan. 22, 1992

Related U.S. Application Data

[63] Continuation of Ser. No. 335,208, Aug. 4, 1989, abandoned.

[30] Foreign Application Priority Data

Jul. 15, 1987 [FR] France .................. 87 10184
Jul. 14, 1988 [EP] European Pat. Off. ........ 88 00639

[51] Int. Cl.⁵ .................................. G01N 23/222
[52] U.S. Cl. .................................. 376/159; 376/163
[58] Field of Search .......................... 376/159, 163

[56] References Cited

U.S. PATENT DOCUMENTS

| | | | |
|---|---|---|---|
| 3,781,556 | 1/1973 | Taylor et al. | 250/302 |
| 3,925,659 | 1/1975 | Paap et al. | 376/163 |
| 3,928,762 | 1/1975 | Peelman | 376/165 |
| 3,930,154 | 1/1975 | Scott | 376/160 |
| 4,028,267 | 6/1977 | Christell et al. | 250/359 |
| 4,361,534 | 11/1982 | Borsaru et al. | 376/159 |
| 4,362,939 | 12/1982 | Horinchi et al. | 250/358.1 |
| 4,582,992 | 4/1986 | Atwell et al. | 250/359.1 |

FOREIGN PATENT DOCUMENTS

| | | |
|---|---|---|
| 295893 | 12/1971 | Austria . |
| 0095900 | 12/1983 | European Pat. Off. . |
| 95900 | 12/1983 | European Pat. Off. . |
| 171256 | 2/1986 | European Pat. Off. . |
| 0171256 | 2/1986 | European Pat. Off. . |
| 1514030 | 2/1968 | France . |
| 2101304 | 1/1983 | United Kingdom . |

*Primary Examiner*—Brooks H. Hunt
*Assistant Examiner*—Frederick H. Voss
*Attorney, Agent, or Firm*—Frost & Jacobs

[57] ABSTRACT

Method for analysis of the content of certain elements in a continuous flow of bulk materials by neutron bombardment and measurement of the gamma radiation emitted by such elements, which makes it possible to distinguish between the capture radiation and the activation radiation. The neutron source is a neutron-generating tube which is activated periodically. The signals from a single gamma radiation detector are considered only after neutron emission has ceased, during distinct intervals corresponding to the phenomena of capture and radiation of the activated elements, respectively. The respective signals are treated in two distinct measurement routes, and the measurements are then combined automatically. A third measurements route can be provided for gamma radiation resulting from inelastic collisions. The source and the detector are positioned in a probe lodged in a polyethylene protective tube within the flow of the materials. The installation is used to analyze large flows of minerals without taking samples, in the mining, cement, and aluminum industries.

21 Claims, 4 Drawing Sheets

METHOD AND INSTALLATION FOR THE ANALYSIS BY NEUTRON ACTIVATION OF A FLOW OF MATERIAL IN BULK

This is a continuation of application Ser. No. 07/335,208, filed Aug. 4, 1989 now abandoned.

BACKGROUND OF THE INVENTION

1. Field of the Invention

The present invention concerns a method for analysis by neutron activation to measure the quantity of one or more elements sought in a flow of material in bulk, in which the flow of material is made to pass close to at least one source of neutrons capable of inducing the emission of gamma rays from said elements, specific gamma rays emitted by the elements are detected, measured and sorted according to their energy spectra, to obtain their respective quantities in the flow of material. The invention also concerns an installation for the application of this method.

1. Description of the Prior Art

A method of this type is known notably in the mining industry, for determining the metal content of ores or the ash content of coal and in cement-making for determining the level of various elements in the raw materials (called the raw feed) which must be gauged for the manufacture of cement. In particular the following publications can be cited EP-A-O 171 256, U.S. Pat. No. 362,939 and WO-84/04393. The method is based on the fact that a bombardment of materials by neutrons causes nuclear reactions with various elements, accompanied by the emission of gamma rays which have different energy levels according to their origin, thus permitting spectrometric analysis. These rays include the so-called capture rays, which are only emitted during the capture of neutrons by atoms thus forming new isotopes, and the so-called activation rays, which are emitted by the radio-active isotopes thus formed and with a decreasing intensity during the life of these isotopes.

Under laboratory conditions, various neutron sources may be used to activate relatively small samples, placed in appropriate containers. But for continuos or intermittent analysis of large quantities in bulk, the size and manoevrability of the source of neutrons limits the possibilities. For such applications on an industrial scale, the standard mathod consists of using a radio-active source to bombard materials passing before it. For example, EP-A-O 171 256 described an installation for neutron activation according to this method and comprising a vertical rectangular funnel into which the bulk materials are continuously fed so as to run from top to bottom at a regular speed, one or more radio-active sources of neutrons arranged on one side of the funnel and one or more detectors arranged opposite the sources on the other side of the funnel in such a way as to obtain the most uniform results possible for the whole of the section of the flow of material.

The fact that radionucleides are permanent sources causes difficulties in such an industrial application. The extensive shielding necessary to protect the human environment, and the risks of contamination by accidental tearing away of the radioactive material of the source, obliges the source to be placed outside the flow of material, irradiation of this being effected by only a fraction of the neutrons emitted by the radionuclides and allowed to flow out of a window in the shielding. This arrangement imposes stringent precautions for the protection of personnel in the vicinity of the installation. Furthermore the section of the funnel therefore the volume of material exposed to the source at a given moment is limited, imposing the need for sampling in the control of large flows of material, such as are found for example in the exploitation or the pre-homogenisation of coal, of iron ore or of cememt raw feed. Also, the gamma ray detectors are exposed to neutron bombardment which may cause damage or deterioration, and to parasitic gamma rays from the two side walls of the funnel which are also the site of nuclear reactions. In addition, to allow for the density of materials in the zone situated between the source of neutrons and the detector opposite. EP-A-O 171 256 shows that extra means must be employed, for example two gamma ray sources situated on either side of the neutron source, and two supplementary detectors situated opposite the gamma ray sources. This increases the complexity of the installation and the problems of protection against radioactivity. Until now these drawbacks have prevented a wide application of the method and of this type of installation.

To limit the problems of radioactive protection, GB-A-2 101 304, in an apparatus designed to sort lumps of gold ore, provides a neutron source in the form of a target carrying deuterium and situated between three vertical rotating funnels arranged in a triangle around the source so as to form three passages for the materials. The target is bombarded with ions by means of a high voltage accelerator situated at the side and linked to the target by a vacuum tube. The gamma rays are detected later on in another part of the apparatus where the pieces are examined individually for sorting. In this way the activated gamma rays are only measured once. In an another side the proposed arrangement of the accelerator and rotating funnels causes considerable constructional difficulties.

Another problem with using radioactive sources is that near the source the gamma rays from capture and activation are measured simultaneously, never individually so that identifying the origin of the rays is made more difficult, even preventing exact measurement of the amounts of certain elements under investigation. The fact that certain activated elements have a very short half-life, of the order of a few seconds, means that a comparison cannot be made with a measure of activation energy made at a certain distance and a certain time after the activation.

SUMMARY OF THE INVENTION

Thus the object of the present invention consists of replacing the radionuclide source by a source from which protection is made easier and which can be used to analyse a stream of material of large capacity, preferably in such a way as to distinguish capture gamma rays from activation gamma rays. An additional object is to provide an analytical method making it unnecessary to measure separately, variable parameters such as density or water content.

With this aim the analytical process according to the invention is characterized in that for the neutron source at least one tube generating neutrons is used, in that the neutron generating tube is used for intermittent periods to produce phases of emission of pulsated flows of neutrons, in that in the time intervals following these impulses the gamma rays from capture and activation by said elements are detected to establish an initial spectrum, in that in at least one other interval of time, gamma rays, from activation only, are detected to establish a second spectrum, and in that the respective values of gamma rays detected in the energy ranges corresponding to the first and second spectra are combined to give an indication of a spectrum containing only gamma rays from capture.

The neutron generating tube is simply turned off to stop the emission of neutrons thus avoiding the risk of irradiating personnel when the apparatus is not in use and also simplifies installation and maintenance. In addition, due to the smaller size of the neutron source and the weak radioactivity of its components, the source (and also the gamma detector) can be placed within the flow of material which thus surrounds it and helps protect against radioactivity. Such an arrangement also has the advantage of being applicable not only to solid granular materials, but also to viscous or liquid flows, for example a slurry consisting of solid matter dispersed in water. Also in contrast to radionuclide sources such as the commonly used Cf-252, a neutron generating tube emits monoenergetic neutrons whose starting energy is higher, for example 14 MeV as opposed to approximately 2.35 MeV for Cf-252. A proportion of the neutrons may be slowed so as to bombard the materials with energy at various levels and so obtain more diverse reactions. This may be achieved by introducing a layer of a substance rich in hydrogen atoms, between the generating tube the flow of material.

Publication EP-A-0 095 900 also describes the use of a neutron generating tube to cause a pulsed bombardment, in combination with means of detecting and measuring gamma rays from capture and activation, but the object and application of this are essentially different from those of the present invention because all that is obtained are the half-lives of the thermal neutrons in geological formations around a drill-hole, for example when one is searching for petrol. The method described in this document does not aim to, nor does it permit measurement of the level of certain elements in the ground around a drill-hole. In fact it necessitates, after each impulse of neutron activation, at least four consecutive intervals of time in which gamma rays are measured, and the decreasing intensity from one interval to the next represents the decrease in the number captured, therefore the decrease in the population of thermal neutrons. These measures are corrected by subtracting the background radiation which is held to be constant and which is measured over a longer interval during which the neutron generating tube is not activated. Not only does this method not give separate meaures of capture and activation gamma rays, neither does it allow any spectral analysis of the rays. Also it necessitates the use of two detectors in the probe introduced in the drill-hole.

In a preferred form of the method, cycles of emission and detection are carried out, which consist of at least one pulsed emission phase comprising regular periods of neutron emission, and regular periods of detection, each emission period being followed by a regular period of detection to pick up the gamma rays from capture and activation, and a phase of non-emission comprising at least one prolonged interval of detection to pick up the gamma rays from activation only, gamma rays detected are measured separately during the regular intervals and the prolonged intervals and these respective measures are combined in such a way as to give and indication of the gamma rays from capture. Each cycle may have a duration of up to 100 ms, whereas the regular intervals of emission and detection are less than 0.2 ms in duration. For each cycle a prolonged interval preferably has a length equal to the sum of the regular detection periods.

In an improvement of this method, pulsed emissions are produced even more rapidly so that after each brief emission the gamma rays produced by the inelastic collisions within the materials under investigation may be detected. During this time the flow of thermal neutrons, therefore the number of captures is negligible. These gamma rays differ from those resulting from capture and activation and may thus provide additional information on the elements under study. To achieve this the cycles consist of two pulsed emission phases, the regular intervals of emission and detection having a time of less than 0.05 ms (preferably of the order of 0.005 ms) in the first phase and of between 0.05 and 0.2 ms in the second phase, the gamma rays detected during the first phase are measured separately and these results are combined with those obtained from the second phase of pulsed emission and from the phase of non-emission so as to give an indication of a spectrum of gamma rays resulting from the inelastic collisions between the neutrons and the elements.

In a particularly useful variation of the method defined by this invention, different energy ranges of gamma rays may be distinguished which are associated with the respective energy levels characteristic of the elements under investigation, the rays detected in these ranges are measured in the relevant channels, and simultaneously in a separate channel are measured the gamma rays detected in a reference range which encompasses all the energies superior to a defined threshold, several of the other ranges being included in this reference range, and an indication of the content of an element in a bulk material is obtained by a linear combination of the measures from the reference range and from the other ranges. Preferably one of the energy ranges should be of 2220 keV, and the threshold should be superior to 2400 keV.

According to the method defined by this invention it is possible to have a material flowing continuously in the zone where the neutron activation and gamma ray detection are carried out.

The flow under analysis may be a stream of solid granular material, or a stream of solid material dispersed in a liquid, usually in the form of a paste or slurry.

In a particular application of the process, the raw feeds for the manufacture of cement are the materials to be analysed. At least one of the following elements may be detected in these materials by means of this invention: carbon, sodium, magnesium, aluminium, silicon, sulphur, calcium, iron. However the method is equally applicable to other processes for measuring the quantities of completely different elements, such as nitrogen, phosphorus or potassium in fertilizer manufacture or of fluorine in the aluminium industry.

To make use of the method defined above, the invention is applied to an installation for neutron activation analysis of a flow of material in bulk comprising a passage for the material, at least one source of neutrons placed close to the passage, at least one gamma ray detector also placed close to the passage, and means of measurement for selectively measuring the characteristic gamma rays emitted by the elements contained in the material. The installation defined by the invention is characterized in that the neutron source is in the form of a tube generating neutrons, in that the installation includes means for controlling in a cyclical manner the flow of neutrons emitted by the generating tube and also means of measuring the emitted gamma rays, and in that the means of measurement consist of at least one channel to measure the gamma rays from activation and capture and another channel measuring only the gamma rays from activation, and means of calculation to combine the measures obtained by the various channels.

One particularly useful form of installation defined by this invention has a single gamma ray detector whose exit is linked to means of switching controlled to transmit signals from the detector exit selectively to one measurement channel, to another one or to none of them, in a sequential manner depending on the pulsed emission cycle of the neutrons.

In the case where the passage of material takes the form of a vertical funnel, a probe containing the neutron generating tube and at least one gamma ray detector may be placed in a protective tube inside the funnel in such a way that the probe is well positioned in the centre of the flow of material. In this arrangement neutrons emitted in all directions by the source come into contact with practically the whole flow of material, except for that part which will be absorbed by a shield placed between the source and the detector. Similarly the detector will receive gamma rays from practically all directions, so effectively that it will be able to correctly detect gamma rays without being "blinded" by the high energy neutrons emitted directly by the source. Preferably the neutron generating tube is arranged in the centre of passage of the materials.

In one particular preferred version of this application, the protective tube surrounding the probe contains a layer of a material rich in hydrogen atoms. Since these atoms have a considerable retarding effect on the neutrons and a particularly large effective section of diffusion, they reduce (by checking the spectrum) the energy of a proportion of the neutrons i.e. the number of thermal neutrons is increased and therefore the number of capture gamma rays. This hydrogen-rich material could be of synthetic origin e.g. polyethylene, in which case the protective tube could be made entirely from this, thus avoiding the use of metal, ceramic or other materials capable of emitting parasitic gamma rays.

Similarly the wall of the funnel could be lined on the interior with a layer of hydrogen-rich material such as polyethylene. Because of its diffusive power this layer sends back into the flow of material a considerable quantity of the neutrons which have not yet been captured. In this way the activation efficiency is improved with respect to the capture and activation in the peripheral zone of the passage of materials.

BRIEF DESCRIPTION OF THE DRAWINGS

In order that the invention will be readily understood, a preferred embodiment will now be described with reference to the annexed diagrams in which.

DETAILED DESCRIPTION OF THE INVENTION

Figure 1:
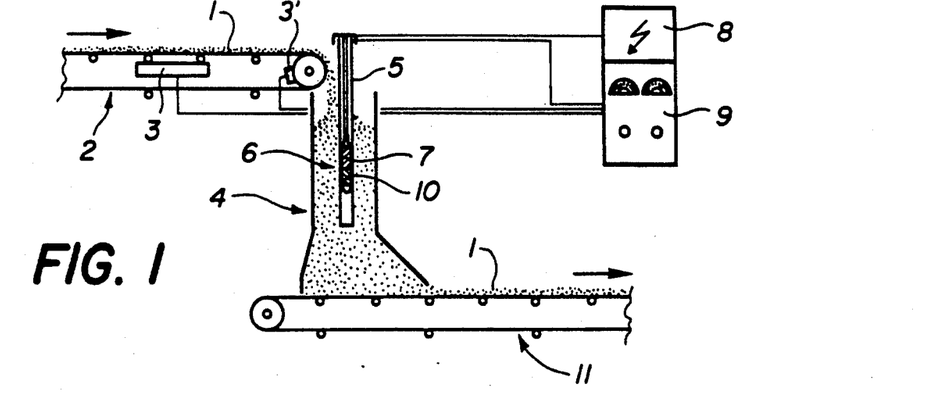
FIG. 1 is a basic outline of the essential parts of an installation based on the invention, for the analysis by neutron activation of solid granular materials in a feed conveying funnel.

With reference to FIG. 1, a flow of material 1 consisting of dry rocks or rocks at natural humidity is destined to be crushed to the required size and to become raw feed for cement manufacture. This material is carried continuously by a belt conveyor 2, equipped with a scale 3 for continuous weighing and tipped into a transfer funnel 4 in which it drops down under the force of gravity and is analysed. It is removed from the base of the funnel by belt conveyor 11 as indicated by the arrows. This arrangement is already known and closely resembles that already described in EP-A-0 171 256.

In the example described here, the funnel 4 contains a central tube 5 arranged vertically and accessible from the top of the funnel. In the part of the tube 5 which is surrounded by the material 1 filling the funnel, a probe 6 containing a neutron generating tube 7 has been placed. This is connected to a high voltage generator by the controller 8 which is connected to a measuring unit 9. The probe also contains a gamma ray detector 10, linked to the measuring unit 9. In this case the detector 10 is a scintillation counter of sodium iodide, but other types of detectors may be used, notably semi-conductor detectors such as bismuth germanate or pure germanium.

The neutron generating tube 7 is commercially available. It consists of a sealed tube containing a source of deuterium ions, a high tension accelerator and a target of titanium charged with tritium on which occurs the following nuclear reaction:

$$H_1^2 + H_1^3 \rightarrow He_2^4 + n_0^1$$

Figure 2:
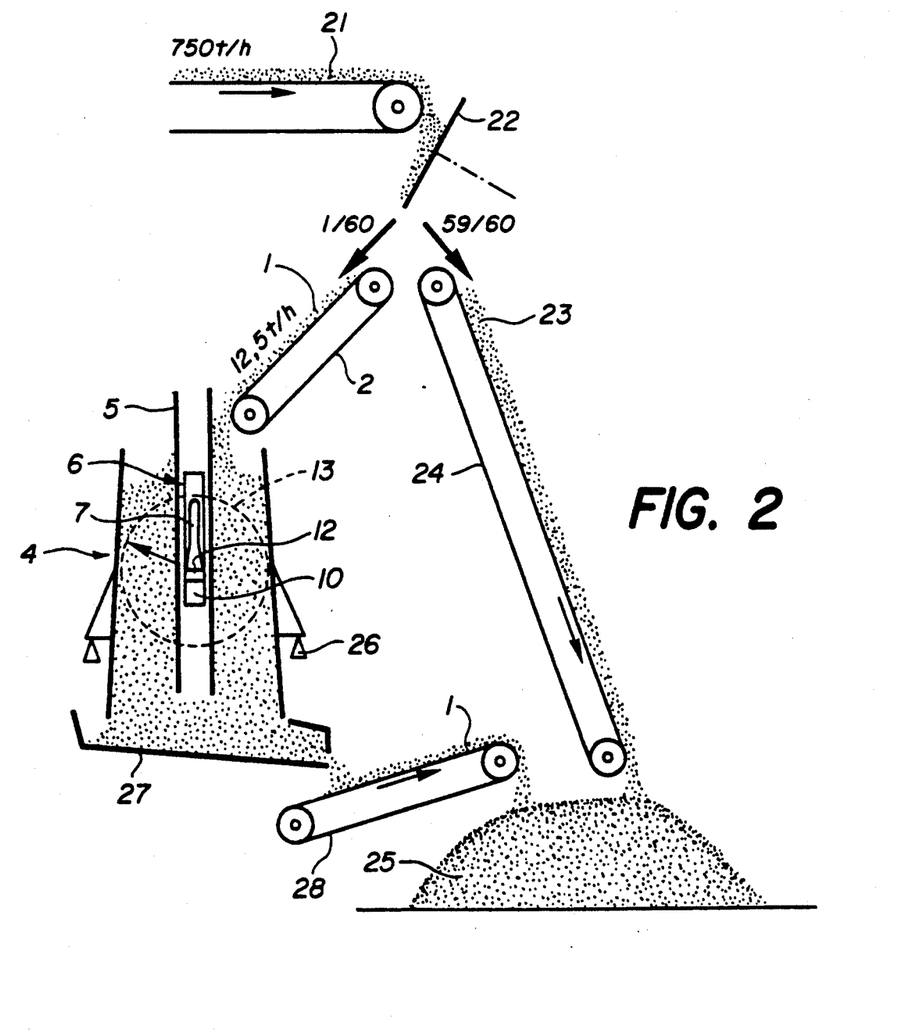
FIG. 2 is a more detailed diagram of the installation, for the case where a sample of the principal flow of the materials is examined.

In a trial installation corresponding to the layout in FIG. 2, a tube with a basic emission rate of $10^8$ neutrons/s in $4\pi$ was used, the initial energy of the electrons being 14 MeV. The range of activity of the neutrons from the target 12 (FIG. 2) is of the order of 30 cm, which corresponds to a relatively large zone of influence 13 and therefore a relatively important section being taken of the material 1 passing through the funnel 4.

Figure 3:
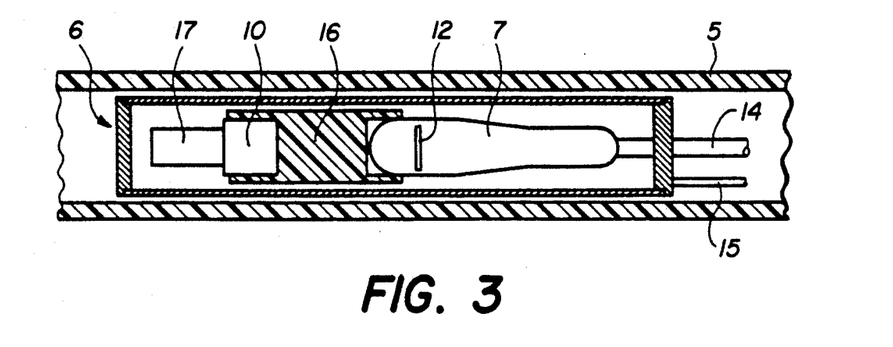
FIG. 3 is a diagram of a probe containing the source of neutrons, in longitudinal section.
Figure 7:
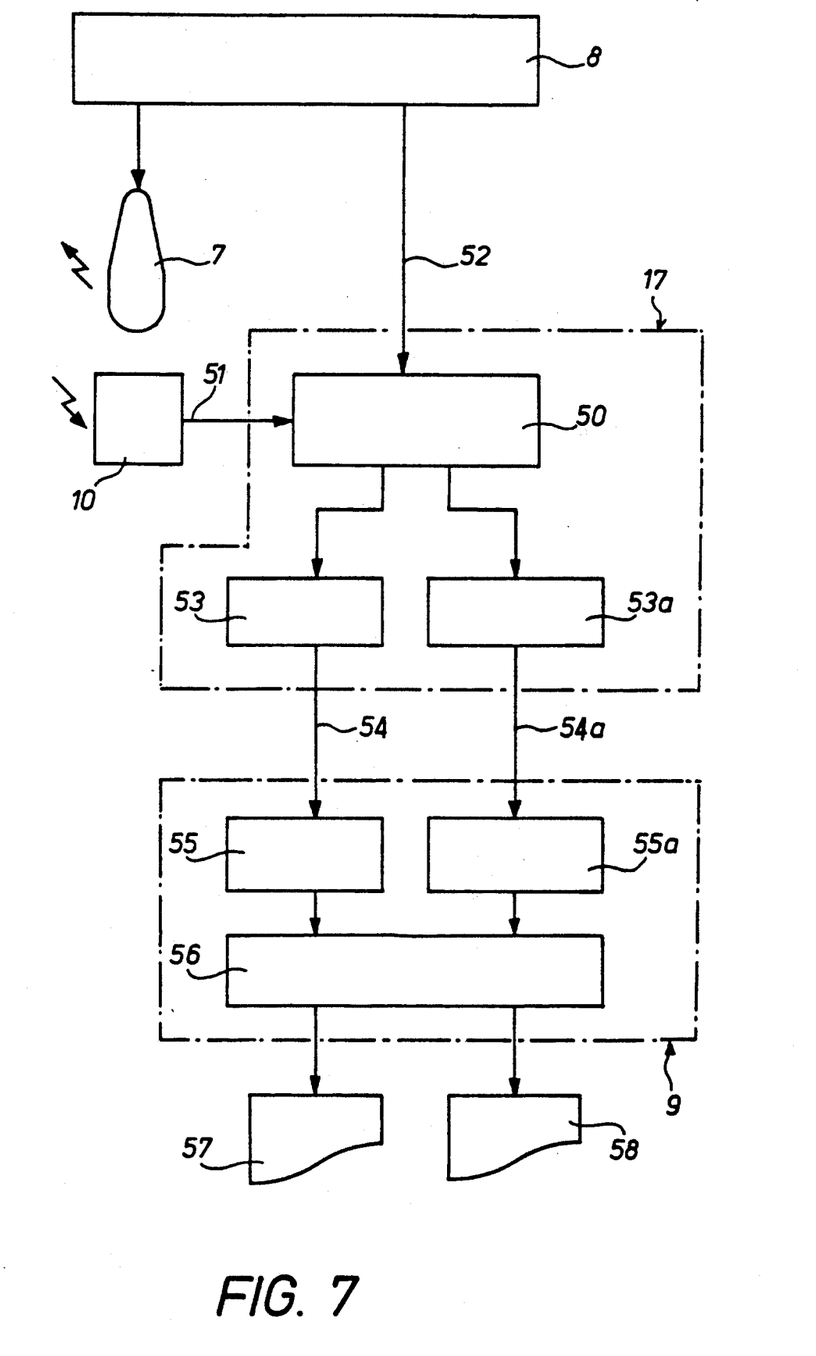
FIG. 7 is a diagram showing two channels for the measurement of gamma rays using only one detector.

FIG. 3 shows a diagram of the probe 6 suspended in the protective tube 5 and linked to the control unit 8 and the measuring unit 9 by cables 14 and 15 respectively. In an outer sleeve of aluminium of approximately 70 mm diameter, the probe 6 comprises, going from top to bottom, the neutron generator 7 with its target 12, shield 16 of polyethylene charged with boron (or some other material) to absorb the neutrons, the detector 10 of sodium iodide and an associated electronic block 17. As shown in FIG. 7, the block 17 contains a switch 50 which receives from one side analogical signals coming from the exit 51 of the detector 10, and on the other side receives via line 52 coming from the controller 8, the command signals to relay the exit signals from the detector to one or another or neither of the two channels of measurement of the gamma rays detected. One channel measures together the rays from capture and activation. In the electronic portion 17 of the probe 6 the channel comprises a multi-channel system of analysis 53 featuring analogue/numerical converters to change the information given into a numerical form on line 54. In the measurement unit 9, this first channel also comprises a multichannel system of analysis 55 in which the signals classed according to the energy of the gamma rays, are counted during pre-determined intervals of time. At moments in the cycle corresponding to the detection of gamma rays of activation only, the switch 50 channels the detection signals to the second measurement channel, which contains electronic components 53a, 54a and 55a similar to 53 to 55 in the first channel.

In measuring unit 9 the signals coming from analysis systems 55 and 55a are treated automatically and simultaneously by the electronic means of calculation 56 according to a normalisation method which will be described later. An essential part of this method is that the values provided by the second channel 53a to 55a are subtracted from the values provided by the first channel 53 to 55 so as to provide figures representing the capture gamma rays only. Thus the calculations of 56 are capable of furnishing the measurements of 57 indicating the levels of certain elements in the materials analysed, measured only from the capture of gamma rays, or the measurements of 58 indicating the levels of other materials, measured only on the basis of activation gamma rays.

The electronic means 50 to 56 described above are known in the field of gamma spectrometry and there is no need to describe them further here. Of course units 53, 55 and 53a and 55a in the different measurement channels may be separated in a different way between the block 17 of the probe and the meauring unit 9.

Figure 4:
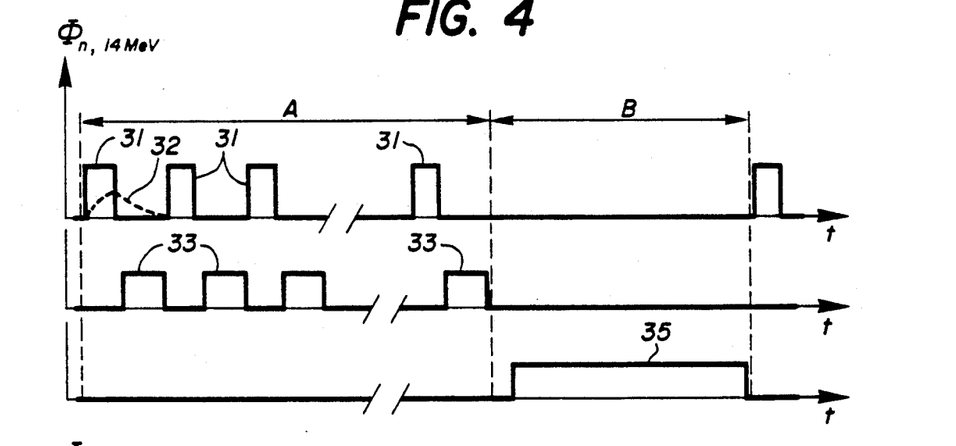
FIG. 4 is a representation of one form of a cycle of neutron emission and of gamma ray detection.

The probe 6 is ordered by control unit 8 to carry out cycles of emission and detection whose length is a fraction of a second e.g. less than 100 ms. In the example of FIG. 4, the cycle has a length of 50 ms. This cycle comprises a phase of pulsed emission A, of 30 ms, followed by a phase of nonemission B, lasting 20 ms. The top diagram of FIG. 4 represents with respect to time, the flux $\Phi n$ of neutrons of 14 MeV emitted by the generating tube. For phase A the generator emits during 100 intervals of 0.1 each separated by a pause of 0.2 ms then the tube stays inactive during phase B. The length of 0.1 ms of the intervals 31 is sufficient to allow the slowing and capture of most of the neutrons. The curve 32 showing the flow of thermal neutrons (shown in dashes and to a different scale) tends to level out after 0.1 ms. The decreasing part of the curve during the 0.2 ms between intervals 31 corresponds to the principal phase of capture of the neutrons. This interval could be shortened in the case of measurements in a humid environment, where the half-life of thermal neutrons is shorter.

The central diagram illustrates, in the form of pulses, regular periods of detection 33 during which the switch 50 (FIG. 7) activates the first channel of measurement of gamma rays 53 to 55 to make use of the indications given by the detector when the neutron generating tube is switched off. Each interval 33 follows an interval 31, but with a delay of approximately 0.05 ms to avoid the detection of gamma rays resulting from inelastic collisions. Here the interval has a length of 0.14 seconds during which it is essentially the capture gamma rays from the beginning of phase A which are detected followed by capture and activation rays. During phase B this first measurement channel is not activated and the switch 50 therefore activates the second channel 53a to 55a (as shown on the lowest diagram in FIG. 4) for a prolonged interval 35, of a length of 14 ms. This length is equal to the sum of the regular intervals 33, and facilitates a comparison between the measurements furnished by the two channels.

By this detection method it is possible to subtract from the measurements of the first channel, the effect due to the activation gamma rays thus directly obtaining a spectrum of capture gamma rays.

Figure 5:
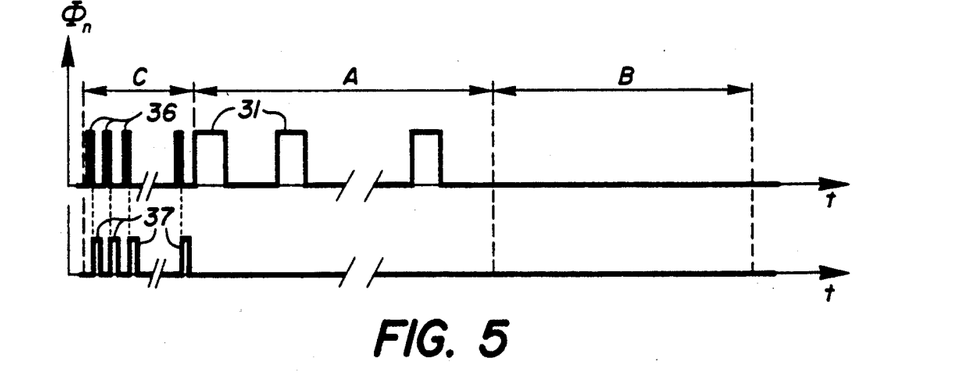
FIG. 5 is a representation of a second form of a cycle of emission and detection

The two diagrams in FIG. 5 correspond to the upper two diagrams of FIG. 4 and illustrate a possibility of using a third measurement channel, for gamma rays resulting from inelastic collisions. This channel may be ranged in the same way as the two channels illustrated in FIG. 7 In this case phase A is preceded by a pulsed emission phase C, comprising a storm of neutrons emitted by the generating tube during the intervals 36. These intervals are sufficiently short that the gamma rays caused by inelastic collisions predominate over those caused by capture. It is important that these intervals are inferior to 50 $\mu$s, if they are less than 5 $\mu$s the number of captures is negligible. The bottom diagram illustrates the intervals of detection covering the free time between the intervals 36. The rays detected during this interval are dealt with in a third measurement channel. Evidently this method requires extremely rapid electronics for the the means of command and measure which are only justified if the capture and activation gamma rays furnish sufficient informations. Owing to the spectral analysis of the "inelastic" gamma rays, one has new possibilities for industrially measuring the level of elements present in relatively low amounts in certain materials, such as the level of carbon in cement raw feed or the level of fluorine in materials involved in the manufacture of aluminium.

In the case illustrated in FIG. 2, the flow of material to be measured is a sample of 1/60th taken from an original flow 21 of 750 t/h of cement raw feed of grain size 0-40 mm, by a disc sampler 22. The flux 1 is fed to the funnel 4 by the conveyor 2, while the rest 23 of the original flow 21 is fed directly, by a conveyor 24, to a pre-homogenisation tank 25 from which materials will be taken for the manufacture of cement.

The silo 4 is equipped with a weighing mechanism 26 which allows the control of filling intermittently or continuously. The weighing also provides useful information for the interpretation of the measurements. A vibrating feeder 27 is positioned under the funnel 4 to allow the material to be drawn off at the desired rate, the extracted materials being evacuated by a conveyor 28 towards the tank 25. The speed of extraction may be adjusted according to the flow.

Two functional modes are possible. In the intermittent mode feeding of the funnel stops when it is full. Then the bombardment may be carried out during a period of less than a minute or several minutes after which the funnel is emptied and may then be refilled.

In a continuous mode filling and emptying of the funnel occur simultaneously and are controlled in such a fashion as to ensure a constant level of material 1 in the funnel. The results of the measurements are interpreted according to an average activation time, rate of flow of the material being determined by means of a scale 3 and of a unit 3' which measures the speed of conveyor 2 as shown in FIG. 1.

Such an installation could also be designed to continuously analyse a very large flow of material, for example the main flow 21 shown in FIG. 2, without too much increase in speed of the material passing by the source 6. To achieve this one would use a funnel with a horizontal section much larger than that of funnel 4 and into which the whole of flow 21 would be directed, by suppressing the sampler 22. One variation involves the arrangement in the funnel of several protective tubes 5 with their respective probes 6 in an optimal manner, always within the flow of material. The counts of gamma photons in the various probes 6 may simply be added together in measuring unit 9.

A second variation consits of using a single large probe 6, placed for example in the centre of this large funnel which is considerably larger than the effective zone of influence 13 of the probe. The materials passing through this zone 13 are considered as being a representative sample of the whole flow. Thus the probe is situated in the very centre of a large mass of material within which there is no risk of the effect of segregation by a boundary. Such an arrangement is also advantageous for the detection of iron, because the protective tube 5 and the probe 6 may be exempt from this metal whereas the walls of the funnel situated out of range of the probe may still be made of steel.

Figure 6:
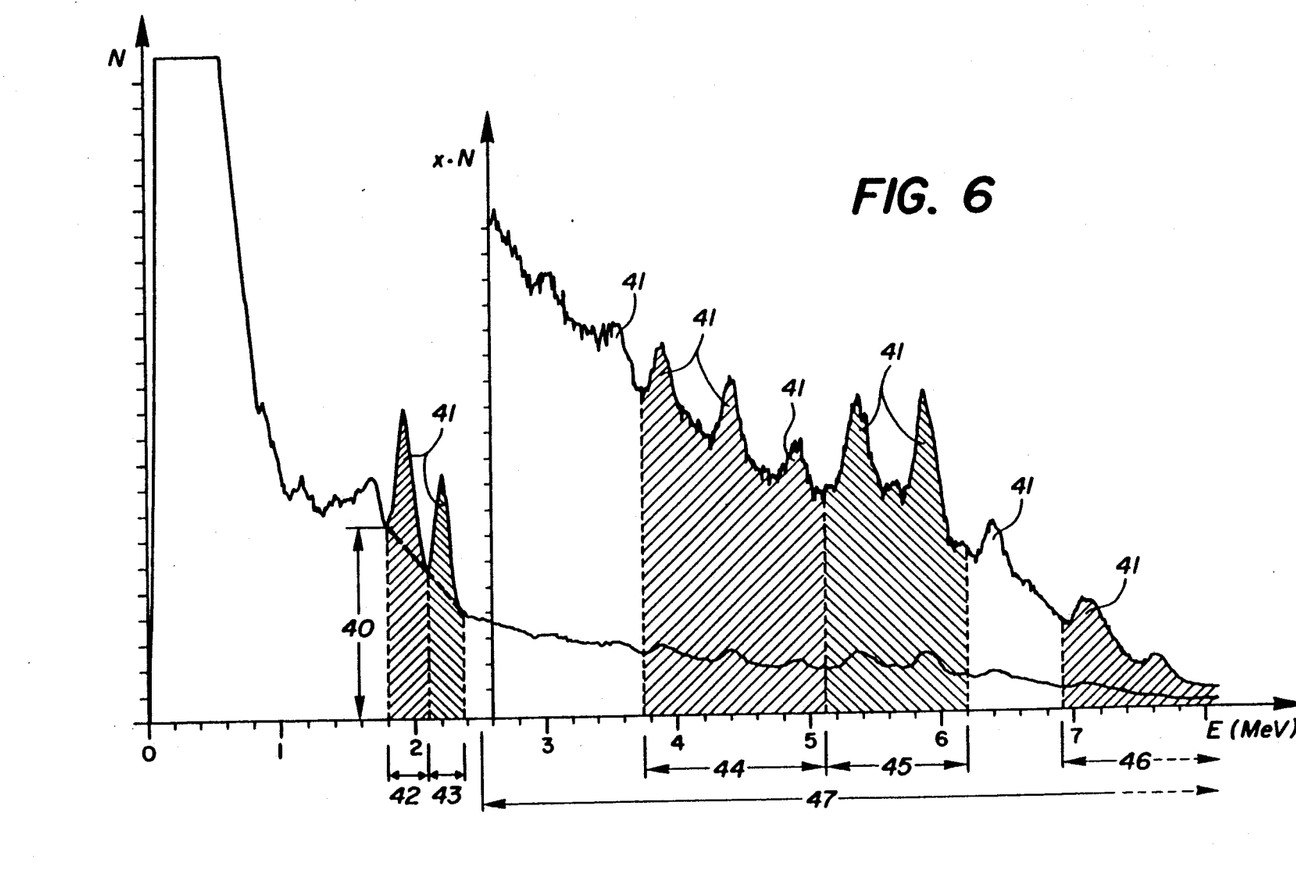
FIG. 6 shows a spectrum of gamma rays from capture.

FIG. 6 shows an example of a spectrum of capture gamma rays and how to utilise this spectrum for the analysis of cement raw feed, in which for example the concentrations of calcium, silicon and iron need to be found. The concentration of aluminium which is of equal importance in the manufacture of cement, will be found by examination of another spectrum showing activation gamma rays. FIG. 6 represents the number N of capture gamma photons detected according to their energy $E = H \cdot v$ during a give time. To facilitate reading of the graph the right hand side of the spectrum has been repeated a second time, enlarged by a factor of x.

Amongst the numerous parameters affecting information received in the form of a spectrum, four are essential:

Ci: concentration of the element i (ponderal fraction) directly proportional to the number of capture reactions produced.

w: water content of the medium.

$\Phi_{th}$: flow of thermal neutrons in the medium irradiated.

$\rho$: density of the material irradiated.

The form of a spectrum thus depends on these parameters, as well as the means of irradiation and detection used, which leads to the assumption of two patterns:

a "Compton background" 40 corresponding to the accumulation of gamma photons having lost energy by Compton diffusion in the flow of material or in the detector;

"photoelectric peaks" 41 observable when the incoming photon loses all its energy in the detector.

The irradiation pulsed by the neutron generating tube and the detection by sodium iodide do not allow the direct separation of the peaks 41 from the Compton background 40. The sodium iodide detector, if it is approximately ten times more efficient than a semi-conductor detector, is however selective and gives peaks which are too pronounced. It is thus necessary to consider the expanded zones of the spectrum, which allow the concentration of an element to be proportioned (Ca, Si, Fe in the present case) to be characterized and also allows the above-mentioned parameters to be taken into account. For this in the interesting zones of the spectrum are defined relatively large ranges of energy 42 to 46 each including at least one peak characteristic of an element required, and also a reference range 47 which corresponds to an integral counting $N_{int}$ of the spectrum for all the energies superior to 2.5 MeV. In the present example, the ranges 42 to 47 correspond to the following characteristics:

| Range | Associated element (keV) | Identification | Energy range (keV) |
| --- | --- | --- | --- |
| 42 | Ca : 1943 | $N_{Ca1}$ | 1810–2090 |
| 43 | H: 2220 | $N_H$ | 2100–2380 |
| 44 | Si: 4930 | $N_{Si}$ | 3750–5130 |
| 45 | Ca: 6420 | $N_{Ca2}$ | 5140–6200 |
| 46 | Fe: 7640 | $N_{Fe}$ | 6800–10000 |
| 47 | Integrale | $N_{int}$ | 2500–10000 |

It must be observed that iron is the only required element figuring in range 46, and that for all the other ranges all the elements present occur with the Compton background. This is deducted by a system of equations in which $f_1$ to $f_3$ represent the functions:

$$N_{Ca} = f_1 (C_{Ca}, C_{Si}, C_{Fe}, O_{th}, w, \rho) \quad (I)$$
$$N_{Si} = f_2 (C_{Si}, C_{Ca}, C_{Fe}, O_{th}, w, \rho)$$
$$N_{Fe} = f_3 (C_{Fe}, \Phi_{th}, w, \rho)$$

The reference range 47 allows the following parameters to be taken into account, $\Phi_{th}$ (flow of thermal neutrons), w(water content), $\rho$(density of material). The count $N_{int}$ increases as the three parameters increase, whether they increase independently or simultaneously. In the case of iron, range 43 associated with hydrogen and representing the water content w must be taken into account, because as w decreases the contribution from the walls of the funnel becomes more important. The concentrations $C_i$ of the elements required are calculated by inversing the equations of system (I) to obtain system:

$$C_{Ca} = g_1 (N_{Ca}, S_{Si}, N_{Fe}, N_{int}) \quad (II)$$
$$S_{Si} = g_2 (N_{Si}, N_{Ca}, N_{Fe}, N_{int})$$
$$C_{Fe} = g_3 (N_{Fe}, N_{int}, N_H)$$

in which $g_1$ to $g_3$ represent functions.

Calculation is finally possible with a linear combination of the respective N values contained for the different elements, the constant term representing the contribution of the environment of the material analysed. System (II) thus takes on the following form:

$$C_{Ca} = (p_1 N_{Ca1} + p_2 N_{Ca2} + p_3 N_{Si} + p_4 N_{Fe})/N_{int} + p_5 \quad (III)$$
$$C_{Si} = (p_1 N_{Si} + p_2 N_{Ca2} + p_3 N_{Fe})/N_{int} + p_4$$
$$C_{Fe} = (p_1 N_{Fe}/N_{int} + p_2 \cdot 1(N_H/N_{int})$$

The coefficients $p_1$ to $p_5$ must be determined by multiple linear regression for the exact experimental conditions after which the proportioning is possible of any element under these conditions.

In the installation described above, such a method of using spectra, also known as a normalisation method, can be made to function automatically by the means of calculation 56 associated with the measuring unit 9 once the coefficients p have been determined. It is seen that by the use of the few relatively large ranges 42 to 47, the number of measurement channels in each channel is greatly reduced.

Even though the example of FIG. 6 refers to capture gamma rays, a similar normalisation method may be applied to the spectra of activation gamma photons, especially for permitting the proportioning of aluminium in the case of cement raw feed. For other applications such as the analysis of carbon or metal ores, the energy ranges will obviously be defined differently depending on which elements are required. A particularly interesting aspect of this method, which applies to all cases, is the elimination of the effect of the water content of the materials which may vary considerably during their extraction and treatment, and also the elimination of the effect of density, unrequired elements and variations in flow of the neutron source.

It is established that the use of neutron bombardment by a neutron generating tube producing pulsed emissions, in comparison with the use of a permanent radioactive source, offers not only a great security, an activation over a wider energy range, and more complete information on the required elements due to the distinction between capture and activation gamma rays, but in addition the disturbing effects existing in previous models such as neutrons reaching the detector, gamma rays caused by neutrons reaching the metal walls and variations due to the density and humidity of the materials, may be easily eliminated. In addition the simultaneous spectrometric analysis of the gamma rays resulting from elastic collisions, in a large flow of material in industrial quantity, has very promising potential, for example for the automatic proportioning of carbonates in the manufacturing of cement.

What is claimed is:

1. In a method for analysis by neutron activation to measure the quantity of one or more elements sought in a flow of material in bulk, comprising a step of neutron bombardment in which the flow of material is made to pass close to at least one source of neutrons capable of inducing the emission of gamma rays from said elements, and a step of gamma ray analysis in which specific gamma rays emitted by the elements are detected, measured and sorted according to their energy spectra, to obtain the respective quantities of said elements in the flow of material, the improvement wherein for the neutron source at least one neutron generating tube is provided, in the step of neutron bombardment the neutron generating tube is electrically actuated for intermittent periods to produce pulsed emission of neutrons, and in the step of gamma ray analysis in the time intervals between said pulses the gamma rays from capture and activation by said elements are detected to establish a first spectrum, and in at least one other interval of time gamma rays, from activation only, are detected to establish a second spectrum, the respective values of gamma rays detected in energy ranges corresponding to said first and the second spectra being combined to give an indication of a spectrum containing only gamma rays from capture.

2. Method according to claim 1, wherein the neutron generating tube and at least one gamma detector are placed in fixed positions within the flow of material.

3. Method according to claim 1, wherein a layer of a substance rich in hydrogen atoms is introduced between the generating tube and the flow of material.

4. Method according to claim 1, wherein cycles of emission and detection are carried out, which include at least one pulsed emission phase comprising regular periods of neutron emission and regular periods of detection of gamma rays, each emission period being followed by a regular period of detection, and at least a phase of non-emission comprising at least one prolonged interval of detection to detect the gamma rays from activation only, gamma rays detected during the regular intervals and the prolonged interval are measured separately, and these respective measures are combined in such a way as to give an indication of the gamma rays from capture.

5. Method according to claim 4, wherein each cycle has a length of up to 100 ms, the regular intervals of emission and detection having less than 0.2 ms in duration.

6. Method according to claim 4 or 5, wherein for each cycle, said prolonged interval has a duration equal to the sum of the regular detection periods.

7. Method according to claim 5, wherein said cycles consists of two pulsed emission phases, the regular intervals of emission and detection have a time of less than 0.05 ms in the first phase and of between 0.05 and 0.2 ms in the second phase, the gamma rays detected during the first phase are measured separately and these measurements are combined with those obtained from the second phase of pulsed emission and from the phase of non-emission so as to give an indication of a spectrum of gamma rays resulting from inelastic collisions between the neutrons and the elements.

8. Method according to claim 1, in which different energy ranges of gamma rays are distinguished which are associated with the respective energy levels characteristic of the elements under investigation, the rays detected in these ranges are measured in the relevant channels, simultaneously in a separate channel, the gamma rays detected in a reference range which encompasses all the energies superior to a defined threshold are measured, several of the other ranges being included in this reference range, and an indication of the content of an element in bulk material is obtained by a linear combination of the measures obtained from the reference range and from the other ranges respectively.

9. Method according to claim 8, wherein one of the energy ranges is 2220 keV, and said threshold is superior to 2400 keV.

10. Method according to claim 1, wherein the material flows continuously through a zone where the neutron activation and gamma ray detection are carried out.

11. Method according to claim 1, wherein said flow is a stream of solid granular material.

12. Method according to claim 1, wherein said flow is a stream of solid material dispersed in a liquid, in the form of a paste or slurry.

13. Method according to claim 1, wherein said materials comprise raw feeds for the manufacture of cement.

14. Method according to claim 13, wherein the elements detected comprise at least one of the following elements: carbon, sodium, magnesium, aluminum, silicon, sulphur, calcium, and iron.

15. Method according to claim 1, wherein the elements detected comprise at least one of the following elements: nitrogen, fluorine, phosphorus and potassium.

16. Installation for neutron activation analysis of one or more elements in a flow of material in bulk, comprising a passage for the material, at least one source of neutrons placed close to said passage, and at least one gamma ray detector also placed close to the passage, said passage being in the form of a vertical funnel having a probe containing one neutron generating tube and at least one gamma ray detector positioned in a protective tube inside said funnel, means of measurement for measuring in selective manner the characteristic gamma rays emitted by elements contained in the material, said neutron source being a tube generating neutrons when it is electrically actuated, wherein the installation comprises means connected to the neutron generating tube for controlling cycles of neutron pulses emitted by the generating tube and also said means of measurement, and wherein said means of measurement comprise at least a first channel to measure the gamma rays from activation and capture and a second channel for measuring only the gamma rays from activation, and means of calculation to combine the measures obtained by said first and second channels.

17. Installation according to claim 16, comprising a single gamma ray detector having an exit linked to means of switching which is controlled to transmit signals from the detector exit selectively to one measurement channel, to another measurement channel, or to neither of them, in a sequential manner depending on the pulsed emission cycle of the neutrons.

18. Installation according to claim 16, wherein said protective tube contains a layer of a material rich in hydrogen atoms.

19. Installation according to claim 16, wherein the wall of said funnel is lined on the interior thereof with a layer of hydrogen-rich material.

20. Installation according to claim 18 or 19, wherein said hydrogen-rich material is polyethylene.

21. Installation according to claim 16 or 17, wherein said neutron generating tube is arranged in the centre of said passage for the material.

* * * * *